(12) United States Patent
Campbell et al.

(10) Patent No.: US 7,320,669 B2
(45) Date of Patent: Jan. 22, 2008

(54) BIOFIDELIC SHOULDER BRACE

(75) Inventors: James H. Campbell, Clarkston, MI (US); Rodger D. Broick, Romeo, MI (US); Bruce G. Kania, Shepherd, MT (US); David L. Zimmerman, Pony, MT (US); Warren Harding, Cincinnati, OH (US)

(73) Assignee: Fountainhead, LLC, Shepherd, MT (US)

( * ) Notice: Subject to any disclaimer, the term of this patent is extended or adjusted under 35 U.S.C. 154(b) by 224 days.

(21) Appl. No.: 11/270,147

(22) Filed: Nov. 9, 2005

(65) Prior Publication Data

US 2007/0106187 A1   May 10, 2007

(51) Int. Cl.
*A61F 5/00* (2006.01)
(52) U.S. Cl. .............................. 602/4; 602/5
(58) Field of Classification Search ............... 602/4–5, 602/19, 20; 128/878, 879, 881
See application file for complete search history.

(56) References Cited

U.S. PATENT DOCUMENTS

| | | | |
|---|---|---|---|
| 1,808,422 A * | 6/1931 | MacDonald | 602/4 |
| 3,277,889 A | 10/1966 | Palmer | |
| 4,446,858 A * | 5/1984 | Verter | 602/4 |
| 4,480,637 A * | 11/1984 | Florek | 602/4 |
| 4,559,932 A | 12/1985 | Salort | |
| 5,018,513 A | 5/1991 | Charles | |
| 5,020,521 A | 6/1991 | Salort | |
| 5,188,587 A * | 2/1993 | McGuire et al. | 602/20 |
| 5,316,547 A | 5/1994 | Gildersleeve | |
| 5,360,394 A | 11/1994 | Christensen | |
| 5,415,625 A | 5/1995 | Cassford et al. | |
| 5,458,565 A | 10/1995 | Tillinghast, III et al. | |
| 5,487,724 A | 1/1996 | Schwenn | |
| 5,520,622 A | 5/1996 | Bastyr et al. | |
| 5,527,267 A | 6/1996 | Billotti | |
| 5,527,268 A | 6/1996 | Gildersleeve et al. | |
| 5,538,499 A | 7/1996 | Schwenn et al. | |
| 5,542,911 A | 8/1996 | Cassford et al. | |
| 5,626,557 A | 5/1997 | Mann | |
| 5,643,185 A | 7/1997 | Watson et al. | |
| 5,792,084 A | 8/1998 | Wilson et al. | |
| 5,865,166 A | 2/1999 | Fitzpatrick et al. | |
| 6,106,493 A * | 8/2000 | Rozell | 602/20 |
| 6,110,133 A * | 8/2000 | Ritts | 602/4 |
| 6,152,891 A * | 11/2000 | Carlson | 602/4 |
| 6,322,528 B1 | 11/2001 | Kania | |
| 6,398,746 B2 | 6/2002 | Bramlage et al. | |
| 6,733,467 B2 | 5/2004 | Kania | |
| 2002/0010409 A1 | 1/2002 | Bramlage et al. | |
| 2002/0022792 A1 | 2/2002 | Kania | |
| 2003/0208146 A1 | 11/2003 | Kania | |
| 2004/0193082 A1 | 9/2004 | Cofre | |

* cited by examiner

*Primary Examiner*—Michael A. Brown
(74) *Attorney, Agent, or Firm*—Antoinette M. Tease

(57) ABSTRACT

A shoulder brace comprising an anterior shoulder support member, a posterior support member, a strap attachment member, three primary straps, three secondary straps, and a pneumatic pad. The posterior support member comprises a back support member and a scapular support member. The back support member preferably comprises a lateral extension, an upper extension and a lower extension. The primary straps are preferably elastic and are used to don the brace. The secondary straps are preferably flexible but not elastic and are used to adjust the position of the anterior shoulder support member over the humeral head of the wearer.

2 Claims, 8 Drawing Sheets

BIOFIDELIC SHOULDER BRACE

BACKGROUND OF THE INVENTION

1. Field of the Invention

The present invention relates to the field of orthopedic braces, and more particularly, to a shoulder brace with a pneumatic pad for increasing or decreasing pressure against the humeral head of the shoulder.

2. Description of the Related Art

The shoulder allows more range of motion than any other joint in the body, and for that reason, it is more susceptible to injury than other joints. Anterior shoulder instability resulting from an initial shoulder disclocation is the primary complaint. In fact, ninety-five percent (95%) of shoulder injuries relate to anterior shoulder instability. Various types of shoulder braces have been developed to prevent or minimize anterior shoulder instability. These braces generally fall into three categories: those that limit the shoulder to a "safe zone" by restricting excessive abduction, extension and external rotation; those that apply a direct force to the shoulder; and those that provide an indirect stabilizing force to the shoulder.

Generally speaking, the first category of braces—those that restrict motion—may be too limiting for certain types of athletic activities. Many of the braces that fall into the second and third categories (i.e., those that apply direct and indirect forces to the shoulder) can hamper athletic function by interfering with respiration, scapulothoracic motion, or muscular excursion. The present invention attempts to overcome all of these limitations. Described below are some of the shoulder braces that have been patented.

U.S. Pat. No. 6,733,467 (Kania, 2004 and U.S. Pat. No. 6,322,528 (Kania, 2001) and U.S. Patent Application Pub. No. 2002/0022792 (Kania) provide a shoulder brace comprising a shoulder joint member and a tension trigger which provides compression or relaxation of the joint member such that a patient's shoulder joint is compressed in an anterior-posterior direction when the patient's arm is moved into a danger zone. The shoulder joint member includes a cushion that is generally aligned with the humeral head, and the brace includes an alignment strap that is wrapped around the patient's chest and pivotally attached to the shoulder joint member. The brace is designed to prevent anterior dislocation of the shoulder joint.

U.S. Patent Application Pub. No. 2003/0208146 (Kania) describes a shoulder brace with front and rear pressure pads that are respectively positioned on the front and rear portions of an individual's shoulder joint. The brace further comprises a support member that is positioned at the wearer's mid-section, and front and rear frame members that are connected to the support member and to the front or rear pressure pad. The brace further comprises an arm cuff and a compression mechanism that compresses the front and rear frame members in accordance with movement of the individual's arm so that the front and rear pressure pads press against the shoulder joint.

U.S. Pat. No. 6,398,746 (Bramlage et al., 2002) discloses a brace for supporting a wearer's shoulder joint during movement. The brace is of one-piece construction, preferably made from a stretchable material. The brace comprises a body sleeve, an inferior strap mechanism (axillary straps), an axillary pouch, and a compression strap (deltoid strap). The axillary pouch and axillary straps create a sling-like mechanism that supports the inferior capsule of the shoulder. Pressure is applied evenly through each end of the deltoid strap to provide compression to the glenohumeral joint. U.S. Patent Application Pub. No. US 2002/0010409 (Bramlage et al., 2002) adds that the axillary straps are positioned in a criss-cross fashion over the acromioclavicular joint and secured in the mid-thoracic spine and mid-sternal regions.

U.S. Pat. No. 6,106,493 (Rozell, 2000) involves a brace for supporting a wearer's shoulder joint during movement. The brace is made of elastic material and comprises a torso strap, a shoulder strap, upper and lower stabilizing straps and a vertical support strap. The upper and lower stabilizing straps, together with the shoulder strap, form a shoulder receiving pocket and help hold the shoulder strap in place.

U.S. Pat. No. 5,487,724 (Schwenn, 1996) provides an orthopedic shoulder brace that is designed to distribute weight evenly onto a patient's waist and hip. The shoulder brace comprises first and second anatomically-conforming shells, each of which has an upper curved portion for fitting around a side of the waist of a user and a lower curved portion for fitting onto the hip of the user. The two shells are connected by a strap in the front and a rotatably connected joining shell in the back. In U.S. Pat. No. 5,538,499 (Schwenn et al., 1996), the brace further comprises a scapulary panel that is worn across the user's back.

U.S. Pat. No. 5,018,513 (Charles, 1991) describes a shoulder brace comprising a pressure-exerting element that is positioned about the human shoulder to exert both anterior-posterior and inferior pressure on the superior aspect of the shoulder. One or more positioning elements are situated around the patient's thorax and attached to the pressure-exerting element to hold it in place. The pressure-exerting element comprises first and second curved members attached at their top ends by a hinge.

U.S. Pat. No. 3,277,889 (Palmer, 1963) discloses a clavicle brace for the treatment of fractures of the clavicle. The device comprises a pair of hoops that are interconnected by straps on the patient's back. A curved, elliptical pad is positioned relatively high up on the anterior portion of each of the patient's shoulders. The pads are attached to the hoops that encircle the patient's shoulders and are preferably made of a soft, pliable layer of felt, sponge rubber, or other similar material. The cover of the pads is preferably a washable, waterproof material such as a synthetic resin or plastic sheet.

Although not a shoulder brace per se, U.S. Pat. No. 5,020,521 (Salort, 1991) and U.S. Pat. No. 4,559,932 (Salort, 1985) involves an apparatus for motor handicaps of the hand of an upper limb of a human, comprising a para-skeleton for the upper limb and hand. The apparatus comprises a shoulder brace formed by at least three semi-rigid shells that are interconnected in a flexible manner. The primary function of this apparatus, however, is not to stabilize the shoulder but to provide mobility of the hand through the use of the scapular motor of the shoulder.

U.S. Patent Application Pub. No. 2004/0193082 (Cofre) provides a position adjustment device that is worn on the shoulder, upper arm and torso of an individual. Specifically, the device is intended to be used to position shoulders in a normal or more normal position in relation to the upper body, compress abnormally protruding scapulas, reduce subluxation or dislocation of shoulders from the shoulder sockets, decrease load on shoulder tissue, and provide abnormal and lower back support. The application covers several different embodiments of the adjustment device, but they all comprise a first securing member (or a first portion), a second securing member (or a second portion), and one or more elongated members that operatively couple the first securing member (or portion) to the second securing member (or portion).

Unlike the patented or patent pending shoulder braces described above, the present invention utilizes a pneumatic pad to increase or decrease pressure on the humeral head. A number of patents involve the use of pneumatic pads in orthopedic braces, but none of these patents does so specifically in the context of a shoulder brace.

U.S. Pat. No. 5,865,166 (Fitzpatrick et al., 1999) discloses an orthopedic cushion or pad that comprises a bladder filled with a combination of spherical objects in a lubricant and an inflatable air bladder. The inflation of the air bladder is used to properly position an orthesis on a patient.

U.S. Pat. No. 5,316,547 (Gildersleeve, 1994) describes an orthopedic brace with one or more pads mounted on it to provide support for the brace when it is positioned against the body of the wearer. Each pad has at least one pneumatic bladder comprised of a flexible skin permanently sealed to enclose a volume of gas within the bladder. In one embodiment, the bladder has a substantially closed-loop configuration. In a second embodiment, the pad is a plurality of interconnected gas-inflated chambers that are maintained in fluid isolation from one another or, alternately, in fluid communication with one another via flow channels. Flexible seams connect the adjacent segments of the pad.

U.S. Pat. No. 5,527,268 (Gildersleeve et al., 1996) involves a hinged orthopedic knee brace with a structural frame and at least one knee condyle pad. The knee condyle pad is configured to conform to the surface of the body overlying the lateral or medial knee condyle and has a fluid-containing primary bladder with a loop configuration encircling a depressed interior opening of the pad.

U.S. Pat. No. 5,792,084 (Wilson et al., 1998) provides a knee brace with a compliant sleeve and a compliant cover overlying an anterior portion of the sleeve. The sleeve and cover are joined around the perimeter of the cover to form a pocket enclosing an inflatable pad. The inflatable pad has a medial chamber and a lateral chamber that are in fluid isolation from each other. The brace is positioned over the knee joint so that the pad circumscribes a portion of the patella, and one or both of the chambers is/are inflated to stabilize the patella.

U.S. Pat. No. 5,626,557 (Mann, 1997) discloses a knee brace with an inflatable bladder and exterior support element. The brace comprises a cloth body with a central knee hole. The cloth body is wrapped around a patient's knee, and hook and loop straps secure the cloth body to the patient. Longitudinally extending pockets on opposite sides of the knee hole contain an air bladder. When inflated, the air bladder supports the patient's knee in rigid position.

U.S. Pat. No. 5,360,394 (Christensen, 1994) describes a removable support brace for supporting a user's limb at the joint. The brace comprises a rigid sheath member with an inner surface and hinging means that allow the sheath member to pivot in concert with the movement of the joint. An array of individually adjustable and inflatable fluid-filled chambers is mounted on the inner surface of the sheath member. The inflatable bladders are used to customize the fit of the brace on the joint.

U.S. Pat. No. 5,520,622 (Bastyr et al., 1996) involves a hinged orthopedic knee brace with a structural frame made up of a plurality of rigid or stiffened support components that are connected to one another by hinges. A plurality of pneumatic pads is attached to the inside faces of the frame to grip the body of the user and simultaneously cushion the body from the frame.

U.S. Pat. No. 5,458,565 (Tillinghast, III et al., 1995) provides an osteoarthritic knee brace with flexible upper and lower arm members rotatably connected to each other by a rotary hinge assembly. An inflatable fluid-containing pad is positioned between the hinge assembly and a side of the knee joint. The pad is used to adjust the force applied to the knee joint by the brace.

U.S. Pat. No. 5,527,267 (Billotti, 1996) discloses a method and brace for supporting a joint of the body to permit movement of the joint in certain directions and to restrain movement in other directions. The brace comprises a flexible sheet and an enclosed inflatable chamber within the flexible sheet. When inflated, the chamber is intended to support the joint and prevent unwanted movement of the portion of the joint to be restrained from movement. The chamber is made of a material that is light and flexible when uninflated but relatively rigid when inflated.

U.S. Pat. No. 5,643,185 (Watson et al., 1997) describes a knee and elbow joint apparatus comprising a bladder chamber and flexible material that wraps around the joint and positions the bladder around the joint. The top of the bladder is covered with a fiber mesh, and reinforcement stays are positioned vertically on each side of the brace apparatus to maintain its shape. The purpose of the bladder is to optimize the support shape around the elbow and knee joints.

U.S. Pat. No. 5,542,911 (Cassford et al, 1996) and U.S. Pat. No. 5,415,625 (Cassford et al., 1995) involve a hinged knee brace with a system of inflatable pads that adjustably provide support for the brace against the leg. Each pad is a pneumatic bladder with a valve that enables inflation or deflation for the purpose of adjusting the fit of the brace to the leg in accordance with the needs of the user.

Through the use of a pneumatic pad, the shoulder brace of the present invention places particular emphasis on maintaining a consistent pressure on the humeral head without restricting motion. This is important because anterior shoulder instability most commonly develops when the restraints of the humeral head are inadequate or excessive force is being applied, usually when the shoulder is in abduction, extension or external rotation. Anterior shoulder stability is usually maintained by the anteroinferior glenohumeral ligament, as well as the subscapularis muscle and the middle glenohumeral ligament. Weakness in these areas allows excessive anterior translation of the humeral head in the glenoid fossa, the humeral head being the ball and the glenoid fossa being the socket of what is commonly referred to as the ball and socket joint of the shoulder. Because the anteroinferior glenohumeral ligament is especially stressed when the arm is positioned in abduction, extension or external rotation, it is reasonable to assume that preventing or limiting these positions might be beneficial for patients with instability. By preventing or limiting those positions, however, athletes who suffer these types of injuries or weaknesses would be particularly impaired in their ability to perform their respective activities.

In light of the above, it is an object of the present invention to provide a shoulder brace that stabilizes the shoulder, and more particular, the humeral head, without impeding the wearer's full range of motion. It is a further object of the present invention to provide a shoulder brace that does not impede respiration, scapulothoracic motion, or muscular excursion during athletic activities. It is a further object of the present invention to provide a shoulder brace that is comfortable, durable, easy to use, and relatively inexpensive to manufacture.

BRIEF SUMMARY OF THE INVENTION

The present invention is a shoulder brace comprising an anterior shoulder support member, a posterior support member, a strap attachment member, three primary straps, three secondary straps, and a pneumatic pad. The anterior shoulder support member comprises an inner surface, and the pneumatic pad is attached to the inner surface of the anterior shoulder support member. The pneumatic pad is positioned directly over the humeral head of the wearer. The pneumatic pad can be inflated or deflated to provide greater or lesser pressure on the humeral head. The pneumatic pad comprises a flexible membrane and one or more inner chambers.

Preferably, the anterior shoulder support member is roughly oval in shape and slightly concave. The anterior shoulder support member and posterior support member are preferably comprised of a rigid and durable material selected from the group consisting of aluminum, polypropylene, polyethylene, composite prepreg materials, and laminated composite materials. The primary straps are preferably comprised of an elastic material. The secondary straps are preferably comprised of a flexible material.

In a preferred embodiment, the posterior support member comprises a back support member and a scapular support member. The back support member preferably comprises a lateral extension, an upper extension and a lower extension, wherein one of the primary straps is permanently attached on one end to the lateral extension of the back support member and removably attached on the other end to the strap attachment member, wherein one of the primary straps is permanently attached on one end to the upper extension of the back support member and removably attached on the other end to the strap attachment member, and wherein one of the primary straps is permanently attached on one end to the lower extension of the back support member and removably attached on the other end to the strap attachment member. The scapular support member is preferably roughly oval in shape and slightly concave. In a preferred embodiment, the scapular support member and the back support member each comprises an outer covering, and the outer covering of the back support member and scapular support member is the same. The back support member is preferably more flexible than the scapular support member.

In a preferred embodiment, two of the secondary straps are permanently attached at one end to the scapular support member and adjustably attached at the other end to the anterior shoulder support member, and one of the secondary straps is permanently attached at one end to the strap attachment member and adjustably attached at the other end to the anterior shoulder support member.

REFERENCE NUMBERS

Figure 1:
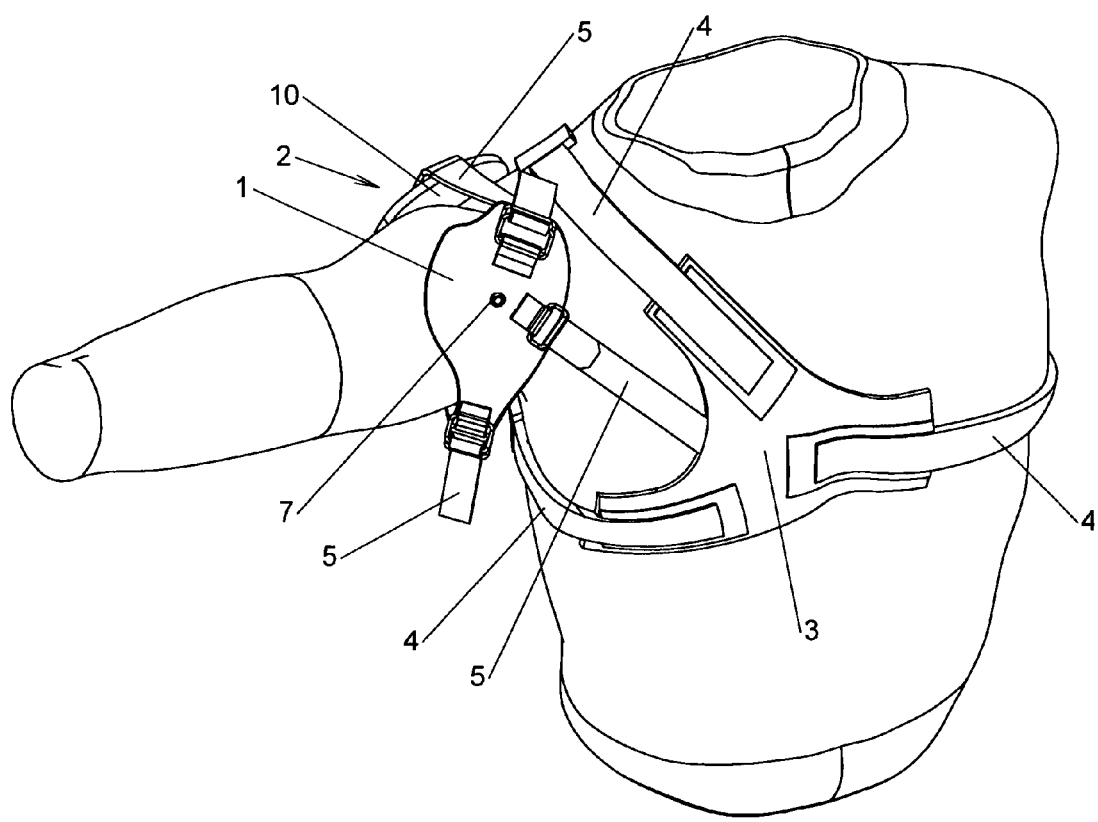
FIG. 1 is a front perspective view of the shoulder brace of the present invention on the wearer.

1 Anterior shoulder support member
2 Posterior support member
3 Strap attachment member
4 Primary strap
5 Secondary strap
6 Pneumatic pad
7 Inflation nipple
8 Flexible membrane
9 Humeral head (on a human shoulder)
10 Scapular support member
11 Back support member
12 Lateral extension (of back support member)
13 Lower extension (of back support member)
14 Upper extension (of back support member)
15 Air pump
16 Inflation chamber (of air pump)
17 Nozzle (of air pump)
18 Spring-loaded plunger (of air pump)
19 Outlet (of air pump)

DETAILED DESCRIPTION OF INVENTION

FIG. 1 is a front perspective view of the shoulder brace of the present invention on the wearer. The shoulder brace of the present invention comprises six main elements. These elements are the anterior shoulder support member 1, the posterior support member 2, the strap attachment member 3, three primary straps 4, three secondary straps 5, and a pneumatic pad 6 (not shown). The pneumatic pad 6 lies on the inner surface of the anterior shoulder support member 1 and is inflatable through an inflation nipple 7 that extends from the pneumatic pad 6 through the anterior shoulder support member 1 and is visible on the front of the brace. The pneumatic pad can be inflated or deflated by a small air pump (see FIGS. 9 and 10) or similar mechanism that can be attached to the air nipple.

The anterior shoulder support member 1 is roughly oval and slightly concave, and it is positioned directly over the humeral head of the shoulder so that it forms a slight cup over the humeral head. The anterior shoulder support member 1 is preferably made of a rigid and durable material, which could be a metal, thermoplastic or composite material. Examples of suitable materials include aluminum, polypropylene, polyethylene, composite prepreg materials, and laminated composite materials. The pneumatic pad 6 (see FIG. 6) is comprised of a flexible membrane 8 and one or more inner chambers. The pneumatic pad 6 is permanently attached to the inner surface of the anterior shoulder support member 1, and it lies in the area between the anterior shoulder support member 1 and the humeral head of the wearer. The pneumatic pad 6 can be inflated or deflated to provide greater or lesser pressure on the humeral head, as desired.

Figure 2:
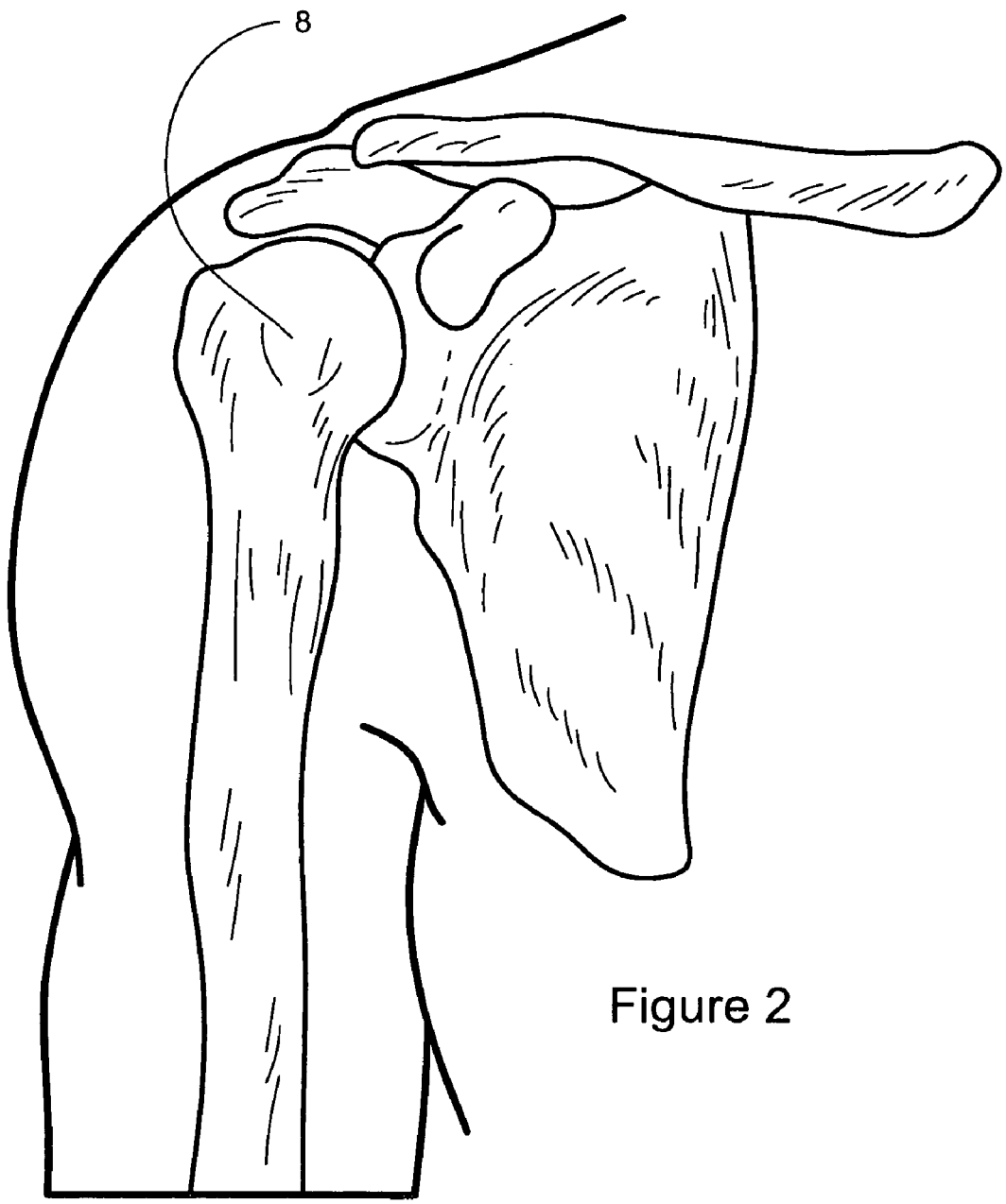
FIG. 2 is an illustration of the anterior aspect of the human shoulder.

FIG. 2 is an illustration of the anterior aspect of the human shoulder. Reference number 8 indicates the position of the humeral head. In the present invention, the pneumatic pad not only applies pressure to the humeral head, but it does so in a manner that allows that pressure to conform to the shape of the humeral head in a manner that a more rigid pressure-exerting device could not. In other words, the pneumatic pad contributes to the brace a biofidelic capacity to conform to the shape of the human body.

The primary straps 4 are preferably made of elastic or other stretchy material. Each primary strap 4 is permanently attached on one end to the posterior support member 2 and removably attached on the other end to the strap attachment member 3, preferably by hook and loop fasteners (with the hooks on the strap attachment member 3 and the loops on the elastic straps 4). The length of the primary straps 4 can be adjusted by pulling them tighter across the strap attachment member 3 or providing more slack. As shown in FIG. 1, one of the primary straps 4 extends from the posterior support member 2 over the wearer's shoulder. Another primary strap extends from the posterior support member 2 under the wearer's arm on the side of the injured shoulder. The third primary strap 4 extends from the posterior support member 2 under the wearer's arm on the opposite side of the wearer. The combination of these three straps makes the shoulder brace easy to put on and easy to remove, even with an injured shoulder.

The strap attachment member 3 is flexible but not elastic, and it is preferably made of an outer covering and an inner padding. The outer covering is preferably made of a fabric or other material that is comfortable to the wearer.

Figure 3:
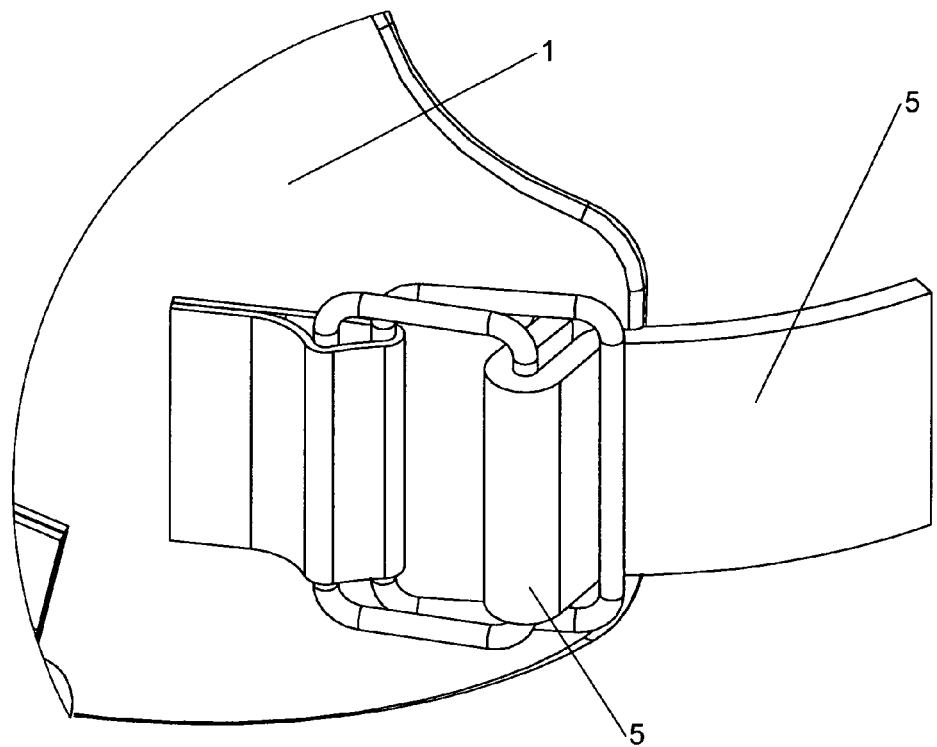
FIG. 3 is a detail view of the double ring-type fastener shown in FIG. 1.
Figure 4:
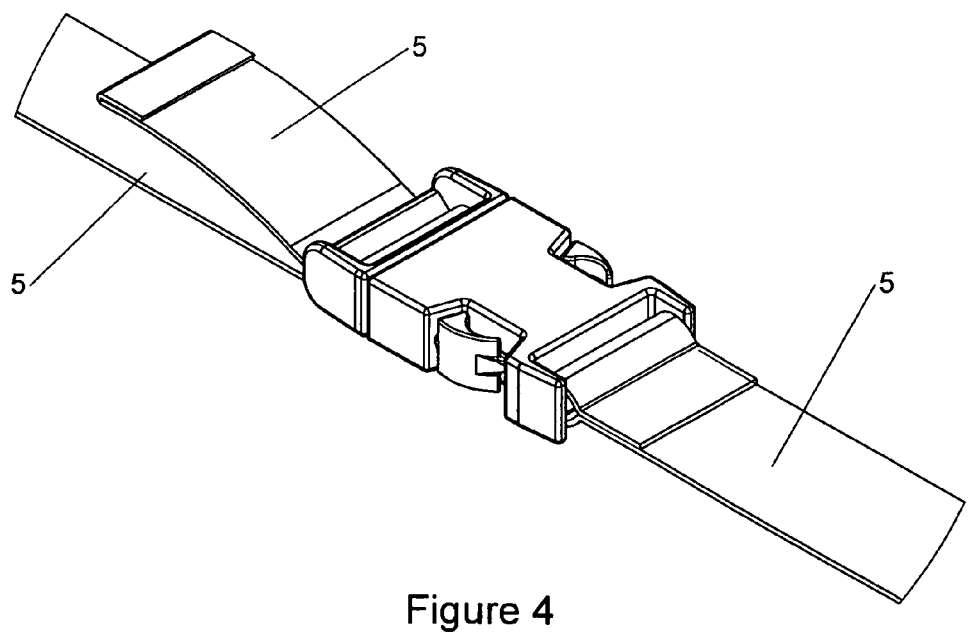
FIG. 4 is a detail view of an alternate fastener.

The secondary straps 5 serve to hold the anterior shoulder support member 1 in place over the humeral head. The secondary straps 5 are preferably not elastic but made of a flexible material. Two of the secondary straps 5 are permanently attached at one end to the posterior support member 2 and adjustably attached at the other end to the anterior shoulder support member 1. The third secondary strap 5 is permanently attached at one end to the strap attachment member and adjustably attached at the other end to the anterior shoulder support member 1. Although FIG. 1 shows the secondary straps 5 attached to the anterior shoulder support member 1 with a double ring-type fastener (see FIG. 3), the present invention is not limited to any particular method of attaching the secondary straps 5 to the anterior shoulder support member 1. Other possible fastening means include buckles (not shown) or pinch-type clasps, such as are used on backpacks and the like (shown in FIG. 4).

Figure 5:
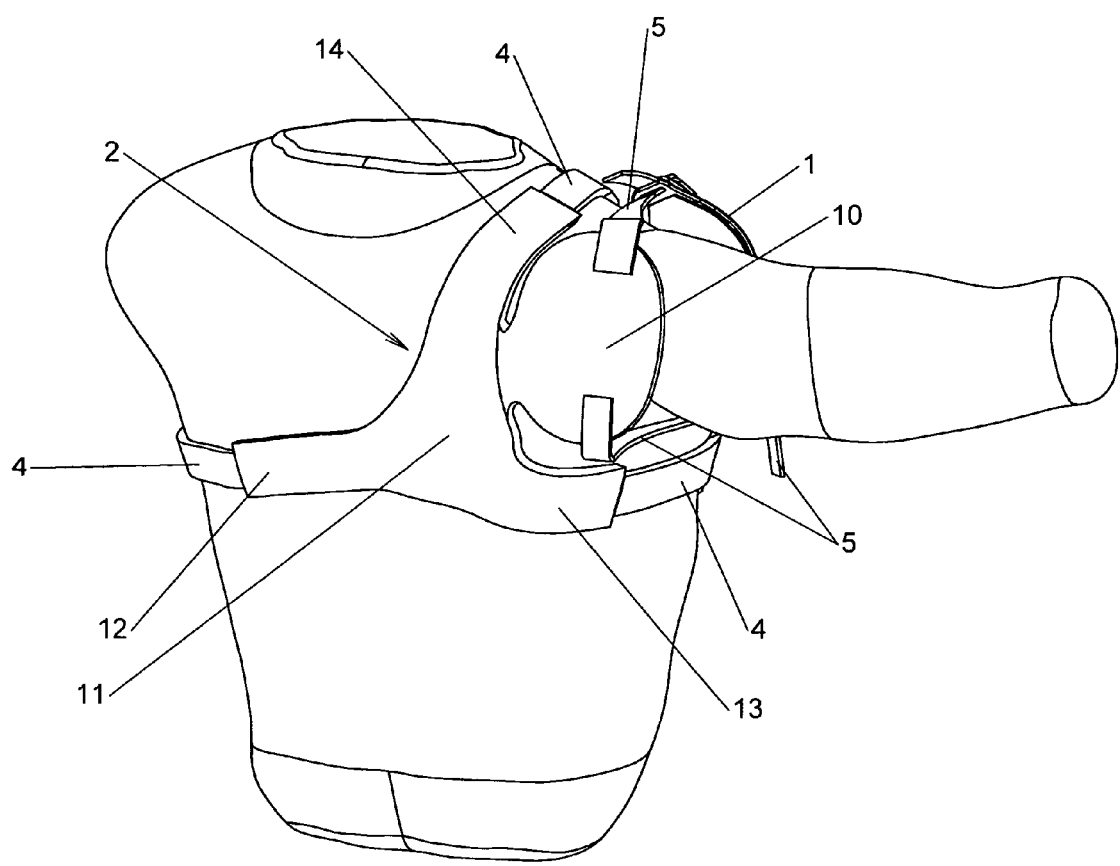
FIG. 5 is a back perspective view of the shoulder brace of the present invention on the wearer.

FIG. 5 is a back perspective view of the shoulder brace of the present invention on the wearer. As shown in this figure, the posterior support member 2 is comprised of a scapular support member 9 and a back support member 10. The scapular support member 9 is preferably made of the same rigid material as the anterior shoulder support member 1, and its shape roughly mimics that of the anterior shoulder support member 1—that is, the scapular support member 9 is preferably oval in shape and slightly concave. The back support member 10 preferably shares the same outer covering as the scapular support member, but it is more flexible than the scapular support member so that it can bend and twist with the user. The back support member 10 comprises a lateral extension 12, a lower extension 13, and an upper extension 14. The upper extension 14 is attached to the primary strap 4 that extends over the wearer's shoulder. The lower extension 13 is attached to the primary strap 4 that extends under the wearer's arm on the side of the injured shoulder. The lateral extension 12 is attached to the primary strap 4 that extends under the wearer's arm on the opposite side of the wearer from the injured shoulder.

Figure 6:
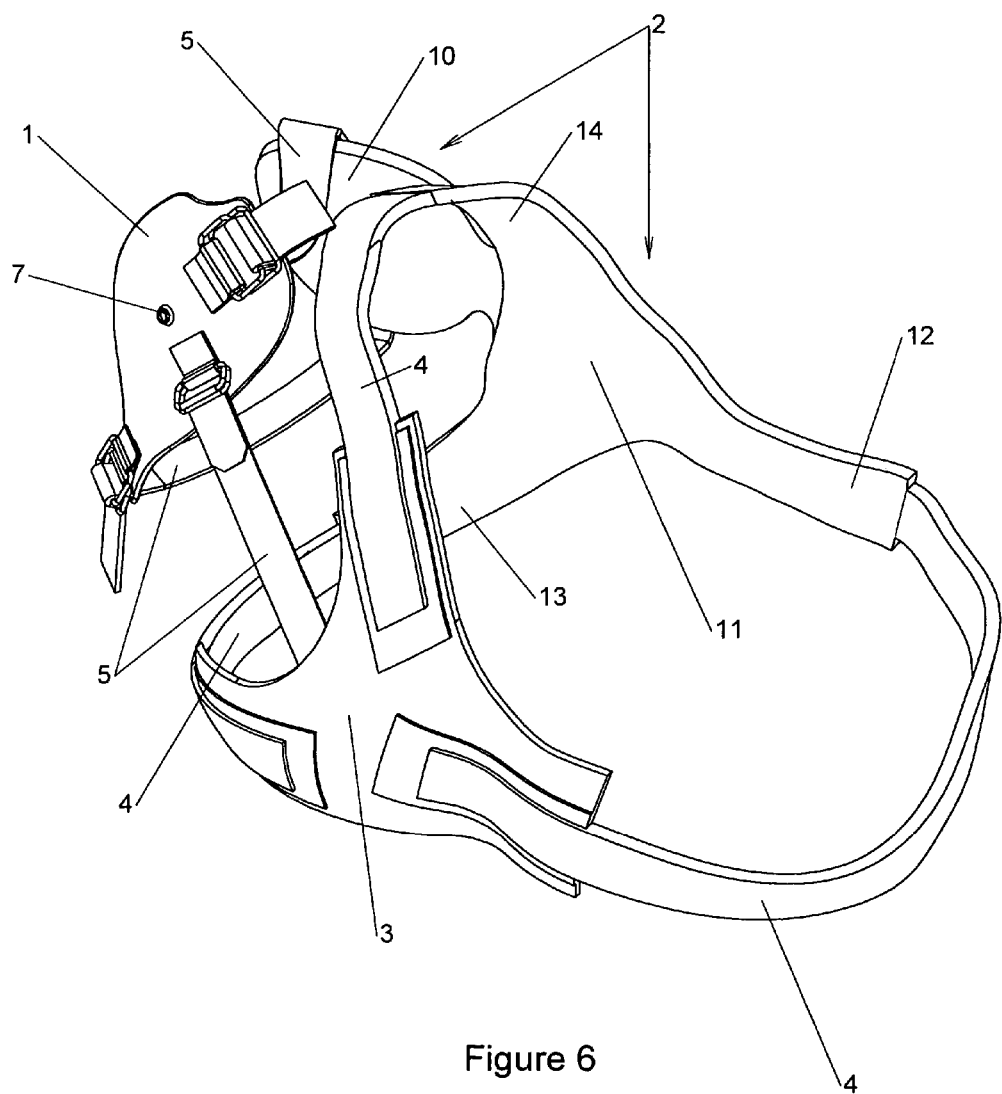
FIG. 6 is a front and side perspective view of the shoulder brace of the present invention.

FIG. 6 is a front and side perspective view of the shoulder brace of the present invention. This figure shows the anterior shoulder support member 1, the posterior support member 2, the strap attachment member 3, the primary straps 4, and the secondary straps 5. It also shows the inflation nipple 7, the scapular support member 10 and the back support member 11.

Figure 7:
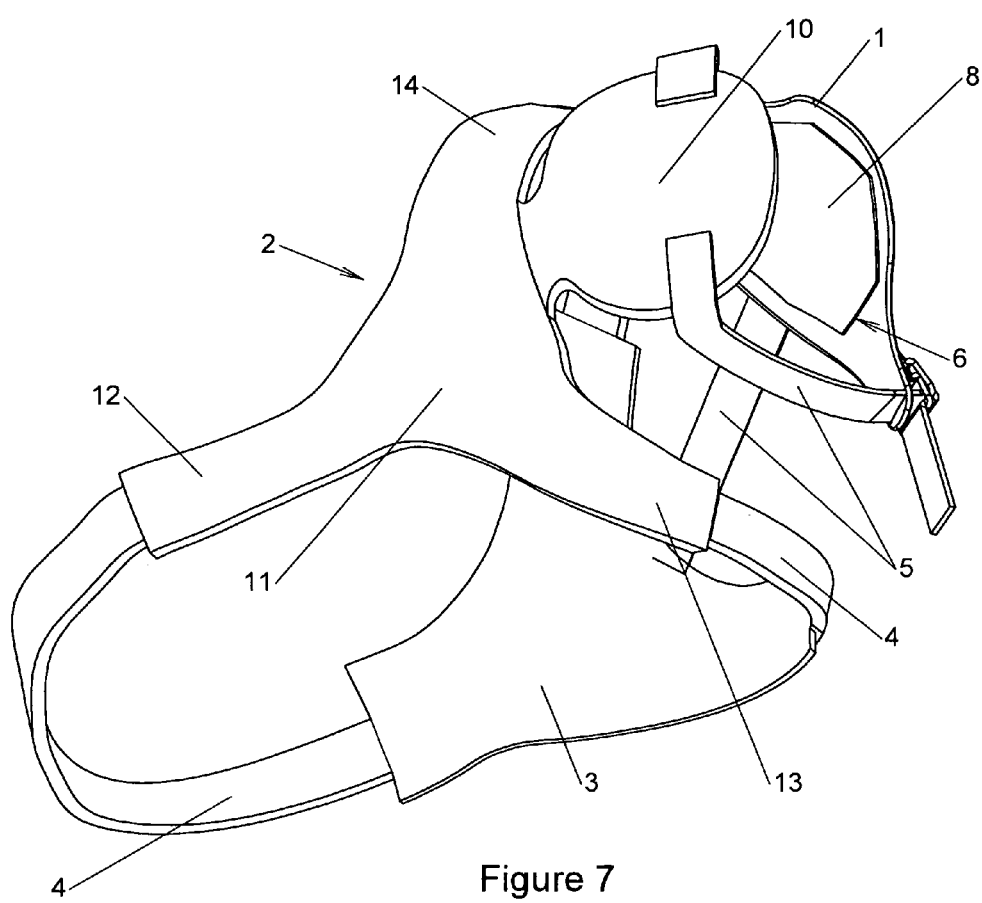
FIG. 7 is a rear and bottom perspective view of the shoulder brace of the present invention.

FIG. 7 is a rear and bottom perspective view of the shoulder brace of the present invention. In addition to the parts shown in FIG. 5, this figure shoes the pneumatic pad 6 on the inner surface of the anterior shoulder support member 1. As described above, the pneumatic pad 6 comprises a flexible membrane 8, which forms one or more inner chambers (not shown) that can be inflated or deflated to suit the needs of the patient and to maintain sufficient pressure on the humeral head.

Figure 8:
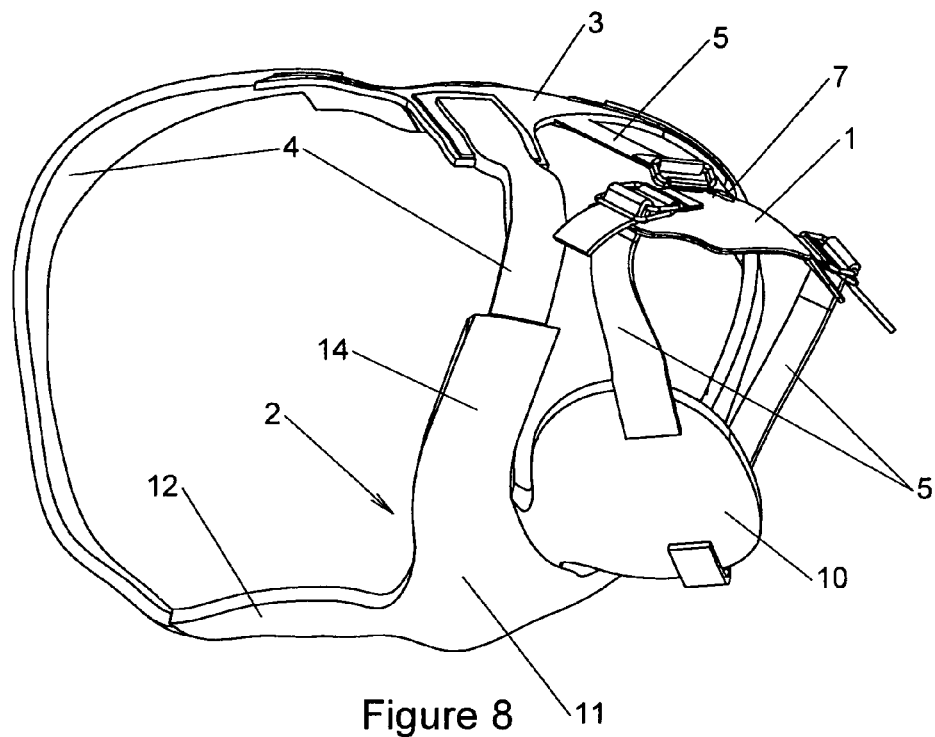
FIG. 8 is a top perspective view of the shoulder brace of the present invention.
Figure 8A:
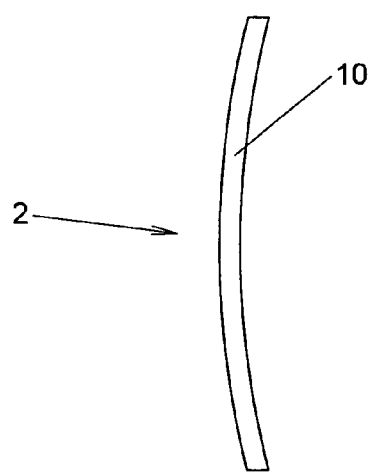
FIG. 8A is a section view of the scapular support member of the present invention.

FIG. 8 is a top perspective view of the shoulder brace of the present invention. This figure shows more clearly the slightly concave shape of the anterior shoulder support member 1. The scapular support member 10 is also slightly concave. FIG. 8A is a section view of the scapular support member, showing the slight concavity of this piece.

Figure 9:
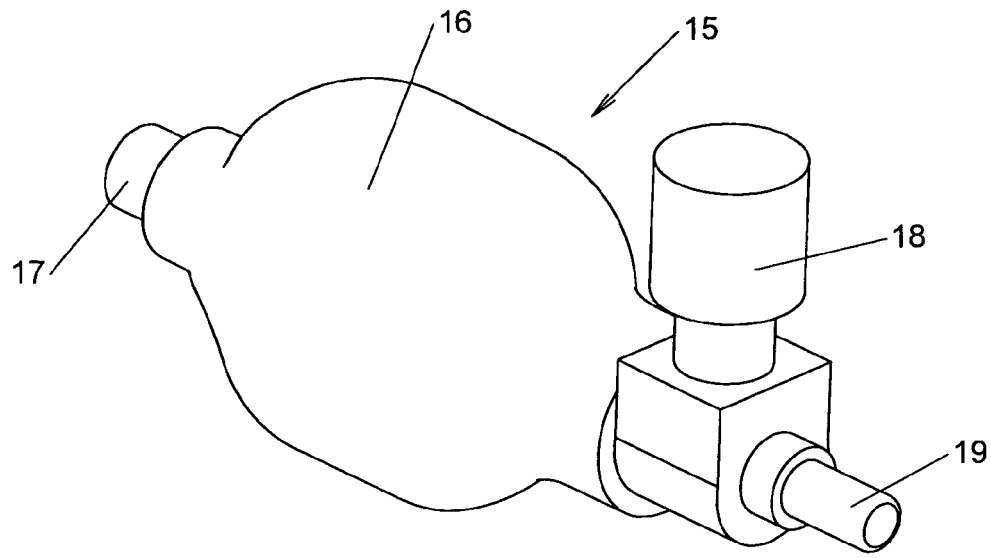
FIG. 9 is a front perspective view of an air pump that can be used in connection with the shoulder brace of the present invention.
Figure 10:
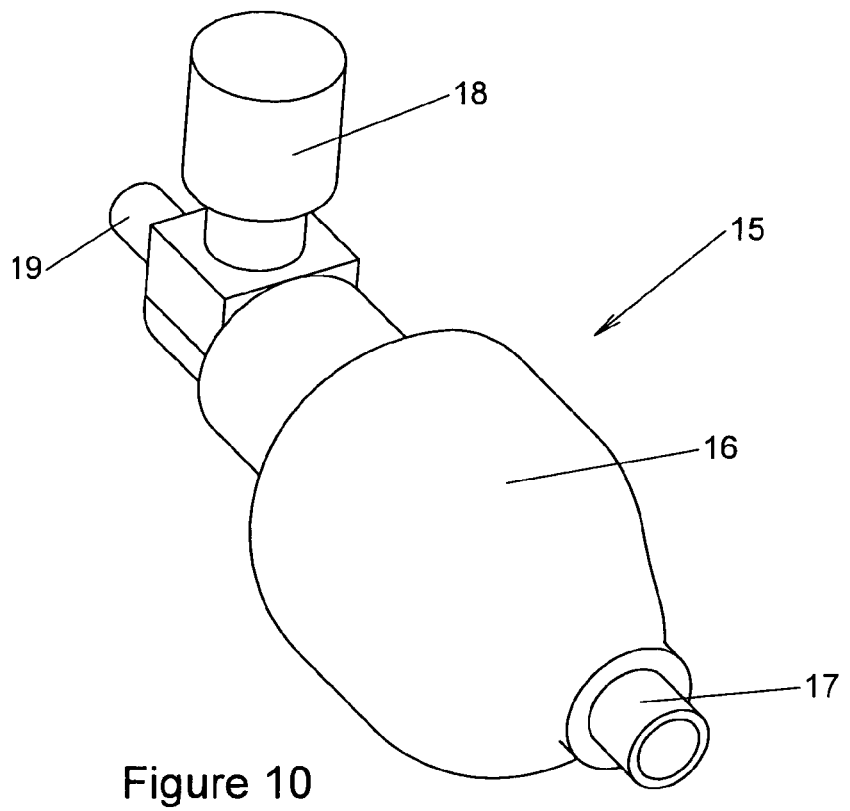
FIG. 10 is a rear perspective view of an air pump that can be used in connection with the shoulder brace of the present invention.

FIGS. 9 and 10 are front perspective and rear perspective views, respectively, of an air pump 15 that can be used in connection with the shoulder brace of the present invention. The present invention is not limited to any particular method of inflating the pneumatic pad, however. In this particular method, the air pump 15 comprises an inflation chamber 16, a nozzle 17, and a spring-loaded plunger 18. To inflate the pneumatic pad 6 (not shown), the nozzle 17 is placed inside the inflation nipple 7 on the anterior shoulder support member 1 (not shown), and the inflation chamber 16 is squeezed manually to inflate the pneumatic pad. To deflate the pneumatic pad, the nozzle 17 is placed inside the inflation nipple 7, and the spring-loaded plunger 18 is depressed, which lets the air out of the pneumatic pad and through the outlet 19.

As is apparent from these figures, the shoulder brace of the present invention does not include an arm cuff or other motion-restricting feature. In fact, a primary challenge of the present invention was to design a shoulder brace that could place the appropriate amount of pressure on the humeral head without using the arm to exert that pressure. The present invention meets that challenge, and it does so with a design that is easy to put on, easy to remove, comfortable to the user, and made of durable materials. In addition, due to the limited number of parts and materials used, the shoulder brace of the present invention is relatively inexpensive to manufacture.

Furthermore, through the use of the pneumatic pad, the shoulder brace of the present invention maintains relatively consistent pressure on the humeral head throughout the full range of motion of the shoulder and without limiting the full range of motion of the wearer. In addition, as is illustrated above, the shoulder brace of the present invention maintains a lower profile than many other braces Although the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A shoulder brace comprising:
   (a) an anterior shoulder support member;
   (b) a posterior support member;
   (c) a strap attachment member;
   (d) three primary straps;
   (e) three secondary straps; and (f) a pneumatic pad;

wherein the posterior support member comprises a back support member and a scapular support member;

wherein the back support member comprises a lateral extension, an upper extension and a lower extension;

wherein one of the primary straps is permanently attached on one end to the lateral extension of the back support member and removably attached on the other end to the strap attachment member.

2. A shoulder brace comprising:

(a) an anterior shoulder support member;

(b) a posterior support member;

(c) a strap attachment member;

(d) three primary straps;

(e) three secondary straps; and (f) a pneumatic pad;

wherein the posterior support member comprises a back support member and a scapular support member;

wherein two of the secondary straps are permanently attached at one end to the scapular support member and adjustably attached at the other end to the anterior shoulder support member; and wherein one of the secondary straps is permanently attached at one end to the strap attachment member and adjustably attached at the other end to the anterior shoulder support member.

* * * * *